United States Patent [19]

Maitra et al.

[11] Patent Number: 5,968,553
[45] Date of Patent: Oct. 19, 1999

[54] PHARMACEUTICAL COMPOSITION CONTAINING BUPROPION HYDROCHLORIDE AND AN INORGANIC ACID STABILIZER

[75] Inventors: Amitava Maitra, Sayreville; Prakash Shriram Kulkarni, Parsippany; Bharat Bhogilal Shah, Ridgefield; Joseph Michael DeVito, Middletown, all of N.J.

[73] Assignee: American Home Products Corporation, Madison, N.J.

[21] Appl. No.: 09/000,673

[22] Filed: Dec. 30, 1997

[51] Int. Cl.$^6$ .......................... A61K 9/28; A61K 31/135
[52] U.S. Cl. .......................... 424/474; 424/464; 424/465; 424/463; 424/490; 514/649; 514/769; 514/970
[58] Field of Search ........................... 424/474, 475, 424/465, 480, 464, 490, 463, 452; 514/970, 769, 649

[56] References Cited

U.S. PATENT DOCUMENTS

| Re. 33,994 | 7/1992 | Baker et al. | 424/465 |
| 3,819,706 | 6/1974 | Mehta | 260/570.5 C |
| 3,885,046 | 5/1975 | Mehta | 424/330 |
| 5,358,970 | 10/1994 | Ruff et al. | 514/649 |
| 5,427,798 | 6/1995 | Ludwig et al. | 424/464 |

*Primary Examiner*—Thurman K. Page
*Assistant Examiner*—James M. Spear
*Attorney, Agent, or Firm*—Rebecca R. Barrett

[57] ABSTRACT

Novel, stable formulations of bupropion hydrochloride are provided which will maintain at least 80% of initial bupropion hydrochloride potency after one year. Methods of inhibiting degradation of bupropion hydrochloride are also provided.

14 Claims, No Drawings

PHARMACEUTICAL COMPOSITION CONTAINING BUPROPION HYDROCHLORIDE AND AN INORGANIC ACID STABILIZER

BACKGROUND OF THE INVENTION

Bupropion hydrochloride is a common antidepressant sold in immediate release, modified release, and extended release tablet forms. See U.S. Pat. Nos. 3,819,706 and 3,885,046. As with many pharmaceuticals, the stability of bupropion hydrochloride is affected by a number of factors including formulation microenvironments and storage conditions.

One formulation of bupropion hydrochloride is taught by Ruff et al., U.S. Pat. No. 5,358,970 to prevent or inhibit degradation of bupropion hydrochloride using one of the stabilizers L-cysteine hydrochloride, glycine hydrochloride, malic acid, sodium metabisulfite, citric acid, tartaric acid and L-cystine dihydrochloride.

DESCRIPTION OF THE INVENTION

In accordance with the present invention is provided a novel pharmaceutical composition comprising bupropion hydrochloride and a pharmaceutically acceptable stabilizer.

Bupropion hydrochloride is disclosed in the aforementioned patents as well as in the *Merck Index,* Twelfth Edition, entry no. 1523.

Stabilizer, as the term is used herein, means a compound which inhibits or prevents the degradation of bupropion hydrochloride so that it can be used in a pharmaceutical formulation while retaining much of its potency. Stabilizers useful in accordance with the present invention retain at least about 80% of the potency of bupropion hydrochloride and preferably over 90% of potency after one year of storage at room temperature (59–77° C.) at 35–60% humidity. Thus, a tablet containing 100 mg of bupropion hydrochloride should retain at least 80 mg and preferably more than 90 mg of bupropion hydrochloride at the end of 1 year in the presence of stabilizers of the present invention.

Suitable stabilizers of the present invention are inorganic acids having an aqueous solution pH of from about 0.5 to about 4.0 at a concentration of about 0.31% w/w.

The stability of the formulation was tested in accordance with industry standards by storage for four to twelve weeks at about 40° C. and about 75% relative humidity. Formulations containing stabilizers of the present invention stored under these conditions retain at least 80% of the bupropion hydrochloride in the composition at the time of storage. In many instance formulations of the present invention retain more than 85% and ideally retain at least 90% of bupropion hydrochloride in the composition at the time of storage. Standard procedures such as HPLC may be used to determine the amount of active ingredient remaining after storage.

The aqueous solution pH of the stabilizers of this invention is determined by adding 15.7 grams of stabilizer to 5084 grams of deionized water in a Pyrex® beaker. The resulting mixture is stirred for approximately 15 minutes, using a stir plate and a magnetic stir bar. The resulting solution is examined using a Corning® pH Meter Model 355. Solutions are stirred with a magnetic stir bar during analysis. Measurements are performed in duplicate and the average thereof is used.

Stabilizers of the present invention include inorganic acids meeting the aforementioned criteria and more specifically include but are not limited to hydrochloric acid, phosphoric acid, nitric acid, and sulfuric acid, or combinations thereof. Hydrochloric acid is a preferred stabilizer.

Pharmaceutical compositions of the present invention may optionally include any conventional ingredients for improving the physical properties, visual appearance or odor of the pharmaceutical. Examples include, but are not limited to, lubricants such as talc; binders such as starch, hydroxypropyl cellulose, hydroxypropyl methylcellulose, polyvinylpyrrolidone; diluents such as microcrystalline cellulose and lactose; disintegrants such as sodium starch glycolate, crospovidone and croscarmellose sodium; and colorants.

The total amount of inactive ingredient in the formulation, including the amount of stabilizer, is preferably more than 50% of the weight of bupropion hydrochloride in the composition and less than 650% of the weight of bupropion hydrochloride. The amount of stabilizer may be from about 0.01% to 5% of the weight of bupropion hydrochloride and is ideally about 0.1% to about 2% of the weight of bupropion hydrochloride in the composition. The suitable amount of stabilizer is based on the label strength of bupropion hydrochloride in the pharmaceutical formulation in solid dosage form and can be determined by one skilled in the art.

Pharmaceutical compositions of the present invention generally contain 25 mg to 500 mg of bupropion hydrochloride. More preferred compositions of the invention contain 50 mg, 75 mg, 100 mg or 150 mg of active ingredient and may be in the form of tablets, caplets or capsules. Immediate, modified, or extended release profiles, or combinations thereof, are encompassed by the present invention.

Pharmaceutical compositions of the present invention are prepared by preparing a dilute solution of inorganic acid and adding the dilute inorganic acid solution to a dry blend of bupropion hydrochloride and other active and inactive ingredients. The mixture is granulated, dried and milled. Solid dosage formulations are prepared such as by compressing the milled granulation to form tablets or caplets. Alternatively, capsules may be prepared by placing the milled granulation in, for example, a two-part hard gelatin capsule.

Solid dosage forms such as the aforementioned may optionally be film coated using an aqueous coating solution or suspension which has been acidified to a pH of about 0.5 to about 4.0. In preferred embodiments of the invention, the aqueous coating solution or suspension is acidified using a dilute inorganic acid such as hydrochloric acid, phosphoric acid, nitric acid, and sulfuric acid to provide an acidic environment on the tablet surface, thereby providing improved stability and further minimizing degradation of bupropion hydrochloride. Dilute, as used herein refers to about 0.095N to about 0.105N and preferably 0.1N.

The following examples are illustrative, but are not limiting of the present invention. Throughout the examples, NF and USP are designations for standards published in the National Formulary and U.S. Pharmacopoeia, respectively.

EXAMPLE 1

The formulation contained the following ingredients in the following amounts:

| Ingredient | Weight per Tablet (mg) 75 mg potency |
|---|---|
| Bupropion Hydrochloride | 75.0 |
| Cellulose, Microcrystalline, NF | 332.0 |
| Talc, USP | 23.0 |
| Hydroxypropyl Cellulose, NF | 10.0 |
| 0.1N Hydrochloric Acid | (0.113 mL) |
| TOTAL | 440.0 |

The ingredients were measured for a 45,000 tablet batch size.

The following ingredients were sifted through a #20 mesh screen:
Cellulose, Microcrystalline, NF
Bupropion Hydrochloride
Hydroxypropyl Cellulose, NF The screened ingredients were transferred to a Collette Gral and mixed for ten (10) minutes, with choppers on for two (2) minutes. The mixed material was granulated with 0.1N Hydrochloric Acid for a granulation time of twelve (12) minutes.

The granulated material was dried in the tray oven at 40 degrees C. to a moisture Loss on Drying (LOD) of 1.5–3.5% w/w. The moisture was measured using a Computrac® moisture analyzer. The granulated, dried material was milled through a model D-6 Fitzmill equipped with a #1 plate, knives forward, at medium speed.

Talc, USP was sifted through a #30 mesh screen into the milled material. The screened and milled material was blended in a Gemco Double Cone Blender for ten (10) minutes. The blended material was compressed on a Kikusui Libra tablet compression machine at a compression weight of about 0.440 grams per tablet.

The compressed tablet cores (22,727) were aqueous film coated using 2833 g of the following coating formulation:

| Opadry White YS-1-7003 | 600 g |
|---|---|
| Purified Water, USP | 3400 g |
| TOTAL: | 4000 g |

The purified water was added to a stainless steel container. To the same container Opadry White was slowly added. The resulting suspension was stirred using a stir bar until uniform and smooth. The tablet cores were coated using a Hi-Coater® 60 tablet coating machine.
Bed Temperature: 38°–40° C.
Inlet Temperature 70° C.
Pan Speed during warming: 1–2 RPM
Pan Speed during coating: 10–11 RPM
Spray Rate: 48 g/min.–53 g/min.

Product stability data were obtained for this formulation stored for 4 weeks at 40° C., 75% relative humidity. Potency was determined using HPLC. Product stability data are presented in Table 1.

TABLE 1

| Weeks | Potency (%) |
|---|---|
| 0 | 100.2 |
| 4 | 88.5 |

EXAMPLE 2

45,000 tablet cores were prepared as described in Example 1 except that the granulated material was dried in the fluid bed dryer in two parts.

The tablet cores were coated as follows:

The formulation for the acidified coating contained the following ingredients in the following amounts:

| Ingredient | Quantity per Tablet |
|---|---|
| Opadry White | 18.7 mg |
| 0.1N Hydrochloric Acid | 0.15 mL |

The coating was prepared as follows:

Opadry White and 0.1N hydrochloric acid were mixed in a stainless steel container for approximately 30 minutes. The tablet cores were coated according to method of Example 1 using the acidified coating suspension. Product stability data were obtained for this formulation stored for 12 weeks at 40° C., 75% relative humidity. Potency was determined using HPLC. Product stability data are presented in Table 2.

Bupropion Hydrochloride—Assay

TABLE 2

| Weeks | Potency (%) |
|---|---|
| 0 | 98.5 |
| 4 | 99.0 |
| 8 | 98.4 |
| 12 | 96.4 |

EXAMPLE 3

The formulation contained the following ingredients in the following amounts:

| Ingredient | Weight per Tablet (mg) 75 mg potency |
|---|---|
| Bupropion Hydrochloride | 75.0 |
| Cellulose, Microcrystalline, NF | 332.0 |
| Talc, USP | 23.0 |
| Hydroxypropyl Cellulose, NF | 10.0 |
| Crospovidone | 25.0 |
| 0.1N Hydrochloric Acid | (0.118 mL) |
| TOTAL | 465.0 |

The ingredients were measured for a 45,000 tablet batch size.

The following ingredients were sifted through a #20 mesh screen:
Cellulose, Microcrystalline, NF
Bupropion Hydrochloride
Hydroxypropyl Cellulose, NF
Crospovidone (64% of total amount)

The screened ingredients were transferred to a 75 liter Collette Gral and blended for ten (10) minutes, with choppers on for two (2) minutes. The blended material was granulated with Hydrochloric Acid for a granulation time of eight (8) minutes.

The granulated material was dried in the fluid bed dryer in two parts to a moisture LOD of 1.5–3.5% w/w. The moisture was measured using a Computrac® moisture analyzer.

The granulated, dried material was milled through a model D-6 Fitzmill equipped with a #1 plate, knives forward, at medium speed.

The milled material was blended in a 2 cu.ft. Gemco Double Cone Blender for ten (10) minutes.

The remaining Crospovidone was sifted through a #20 mesh screen into the milled material. The screened and milled material was blended in the Gemco Double Cone Blender for five (5) minutes. Thereafter, talc, USP was sifted through a #30 mesh screen into the blended material. The screened and milled material was blended in the Gemco Double Cone Blender for ten (10) minutes. The blended material was compressed on a Kikusui Libra tablet compression machine at a compression weight of about 0.465 grams per tablet.

The compressed tablet cores were aqueous film coated using the following coating formulation:

| Ingredient | Quantity per Tablet |
| --- | --- |
| Opadry White YS-1-7003 | 18.7 mg |
| 0.1N Hydrochloric Acid Solution | 0.15 mL |

The coating suspension was prepared as follows:

The 0.1N Hydrochloric Acid solution was added to a container. To the same container, Opadry White was slowly added. The resulting suspension was stirred using a stir bar until uniform and smooth.

The tablet cores were coated according to the procedure described in Example 1 using a Hi-Coater® 60 tablet coating machine.

Tablet cores were coated to an approximate weight of 0.480 grams.

Product stability data were obtained for this formulation stored for 12 weeks at 40° C., 75% relative humidity. Potency was determined using HPLC. Product stability data are presented in Table 3.

TABLE 3

| Weeks | Potency (%) |
| --- | --- |
| 0 | 97.6 |
| 4 | 99.5 |
| 8 | 98.8 |
| 12 | 97.2 |

EXAMPLE 4

The formulation contained the following ingredients in the following amounts:

| Ingredient | Weight per Tablet (mg) 100 mg potency |
| --- | --- |
| Bupropion Hydrochloride | 100.0 |
| Cellulose, Microcrystalline, NF | 442.7 |
| Talc, USP | 30.7 |
| Hydroxypropyl Cellulose, NF | 13.3 |
| Crospovidone | 33.3 |
| 0.1N Hydrochloric Acid | (0.083 mL) |
| TOTAL | 620.0 |

The ingredients were measured for a 42,000 tablet batch size.

The following ingredients were sifted through a #20 mesh screen:
Cellulose, Microcrystalline, NF (50% of total)
Bupropion Hydrochloride
Hydroxypropyl Cellulose, NF
Crospovidone (64% of total)

The screened ingredients were transferred to a Collette Gral and blended for ten (10) minutes, with choppers on for two (2) minutes.

The blended material was granulated with Hydrochloric Acid for a granulation time of approximately 5–6 minutes.

The granulated material was dried in the fluid bed dryer to a moisture LOD of 1.5–3.5% w/w.

The moisture was measured using a Computrac® moisture analyzer.

The granulated, dried material was milled through a model D-6 Fitzmill equipped with a #1 plate, knives forward, at medium speed.

The remaining cellulose microcrystalline, NF and crospovidone were screened through a #20 mesh screen. The screened and milled material was blended in a Gemco Double Cone Blender for ten (10) minutes.

The talc, USP was screened through a #30 mesh screen:

The screened and milled materials were blended in a Gemco Double Cone Blender for ten (10) minutes.

The blended material was compressed on a Kikusui Libra tablet compression machine at a compression weight of about 0.620 grams per tablet.

Product stability data were obtained for tablet cores prepared according to this formulation stored for 12 weeks at 40° C., 75% relative humidity. Potency was determined using HPLC. Product stability data are presented in Table 4.

TABLE 4

| Weeks | Potency (%) |
| --- | --- |
| 0 | 99.1 |
| 4 | 99.7 |
| 8 | 97.2 |
| 12 | 98.8 |

EXAMPLE 5

The formulation was prepared as described in Example 4 using 100 mg of bupropion hydrochloride per tablet core. The granulated material was dried to a moisture LOD of 1.5–3.5% w/w. The blended material was compressed on a Kikusui Libra tablet compression machine at a compression weight of about 0.620 grams per tablet. Tablet cores were coated according to the procedure listed in Example 2 using Chromatone® P instead of Opadry White.

The formulation for the acidified coating contained the following ingredients in the following amounts:

| Ingredient | Quantity per Tablet |
|---|---|
| Polyethylene Glycol, NF | 1.6 mg |
| Polysorbate 80, NF | 0.2 mg |
| Chromatone ® P DDB 8440-OR | 17.9 mg |
| 0.1N Hydrochloric Acid | (0.11 mL) |

The coating was prepared as follows:

The 0.1N hydrochloric acid was transferred to a stainless steel container with a mixer. Polysorbate 80, NF, Polyethylene glycol, NF and Chromatone® P DDB 8440-OR were added to the container. The resulting acidified coating suspension was stirred during this Step and for approximately 30 minutes before use. The tablet cores were coated according to method of Example 1 using the acidified coating suspension.

Product stability data were obtained for this formulation stored for 4 weeks at 40° C., 75% relative humidity. Potency was determined using HPLC. Product stability data are presented in Table 5.

TABLE 5

| Weeks | Potency (%) |
|---|---|
| 0 | 97.5 |
| 4 | 99.6 |

EXAMPLE 6

The formulation contained the following ingredients in the following amounts:

| Ingredient | Weight per Tablet (mg) 100 mg potency |
|---|---|
| Bupropion Hydrochloride | 100.0 |
| Cellulose, Microcrystalline, NF | 420.2 |
| Talc, USP | 30.7 |
| Hydroxypropyl Cellulose, NF | 13.3 |
| Crospovidone, NF | 55.8 |
| 0.1N Hydrochloric Acid | (0.083 mL) |
| TOTAL | 620.0 |

The ingredients were measured for a 42,000 tablet batch size.

The following ingredients were sifted through a #20 mesh screen:
Cellulose, Microcrystalline, NF (50% of total)
Bupropion Hydrochloride
Hydroxypropyl Cellulose, NF
Crospovidone, NF (55% of total)

The screened ingredients were transferred to a Collette Gral and blended for ten (10) minutes, with choppers on for two (2) minutes. The blended material was granulated with Hydrochloric Acid for a granulation time of approximately 5–6 minutes.

The granulated material was dried in two parts in the fluid bed dryer to a moisture LOD of 1.5–3.5% w/w.

The moisture was measured using a Computrac® moisture analyzer.

The granulated, dried material was milled through a model D-6 Fitzmill equipped with a #0 plate, knives forward, at medium speed.

The remaining cellulose microcrystalline, NF and crospovidone were screened through a #20 mesh screen.

The screened and milled material was blended in a Gemco Double Cone Blender for ten (10) minutes. Thereafter the talc, USP was screened through a #30 mesh screen. The screened and milled material was blended in a Gemco Double Cone Blender for ten (10) minutes.

The blended material was compressed on a Kikusui Libra tablet compression machine at a compression weight of about 0.620 grams per tablet. Tablet cores were coated according to the procedure described in Example 5. Product stability data were obtained for this formulation stored for 8 weeks at 40° C., 75% relative humidity. Potency was determined using HPLC. Product stability data are presented in Table 6.

TABLE 6

| Weeks | Potency (%) |
|---|---|
| 0 | 96.7 |
| 4 | 97.6 |
| 8 | 95.3 |

What is claimed is:

1. A pharmaceutical composition in solid form comprising bupropion hydrochloride and a pharmaceutically acceptable stabilizer in an effective stabilizing amount wherein said stabilizer is an inorganic acid having an aqueous solution pH of about 0.5 to about 4.0 at a concentration of about 0.31% w/w.

2. A method for stabilizing bupropion hydrochloride in solid form comprising mixing a pharmaceutically effective amount of bupropion hydrochloride with an effective stabilizing amount of a stabilizer wherein said stabilizer is an inorganic acid having an aqueous solution pH of about 0.5 to about 4.0 at a concentration of about 0.31% w/w, such that said composition retains at least 80% of its initial potency after storage for about 12 weeks at about 40° C. and about 75% relative humidity.

3. The composition of claim 1 wherein the stabilizer is selected from the group consisting of hydrochloric acid, phosphoric acid, nitric acid and sulfuric acid.

4. The composition of claim 3 wherein the stabilizer is hydrochloric acid.

5. The composition of claim 1 wherein the amount of stabilizer in the composition is from about 0.01% to about 5.0% of the amount of bupropion hydrochloride in the composition.

6. The composition of claim 5 wherein the composition comprises from about 50 mg to about 300 mg of bupropion hydrochloride.

7. The composition of claim 1 further comprising a film coating wherein said film coating is acidified to a pH of from about 0.5 to about 4.0.

8. The composition of claim 7 wherein said film coating is acidified using an inorganic acid.

9. The composition of claim 8 wherein the stabilizer is selected from the group consisting of hydrochloric acid, phosphoric acid, nitric acid and sulfuric acid.

10. The composition of claim 9 wherein the inorganic acid is hydrochloric acid.

11. The method of claim 2 further comprising forming a solid dosage form and coating the solid dosage form with an acidified film coating solution or suspension having a pH in the range of about 0.5 to about 4.0.

12. The method of claim 2 wherein the stabilizer is selected from the group consisting of hydrochloric acid, phosphoric acid, nitric acid and sulfuric acid.

13. The method of claim 12 wherein the stabilizer is hydrochloric acid.

14. The method of claim 11 wherein the film coating is acidified using an inorganic acid.

* * * * *